US 7,244,435 B2
Jul. 17, 2007

(12) United States Patent
Lai

(10) Patent No.: US 7,244,435 B2
(45) Date of Patent: Jul. 17, 2007

(54) DNA VACCINE EXPRESSING HA1 OF EQUINE-2 INFLUENZA VIRUS

(75) Inventor: Alexander Lai, Stillwater, OK (US)

(73) Assignee: Board of Regents for Oklahoma State University, Stillwater, OK (US)

( * ) Notice: Subject to any disclaimer, the term of this patent is extended or adjusted under 35 U.S.C. 154(b) by 0 days.

(21) Appl. No.: 10/826,929

(22) Filed: Apr. 16, 2004

(65) Prior Publication Data

US 2005/0032732 A1 Feb. 10, 2005

Related U.S. Application Data

(60) Provisional application No. 60/470,843, filed on May 15, 2003.

(51) Int. Cl.
*A61K 39/145* (2006.01)
*A61K 35/12* (2006.01)

(52) U.S. Cl. .................. 424/210.1; 424/186.1; 435/235.1

(58) Field of Classification Search .......... 424/209.1, 424/210.1, 204.1, 186.1, 450, 199.1; 514/44; 435/320.1; 536/23.72
See application file for complete search history.

(56) References Cited

U.S. PATENT DOCUMENTS

| 4,619,827 A | 10/1986 | Bull et al. ............. 424/89 |
| 4,631,191 A | 12/1986 | Dale et al. ............. 424/88 |
| 4,683,137 A | 7/1987 | Coggins et al. .......... 424/89 |
| 4,689,224 A | 8/1987 | Bull et al. ............. 424/89 |
| 4,693,893 A | 9/1987 | Campbell ............... 424/89 |
| 4,920,213 A | 4/1990 | Dale et al. ............. 536/27 |
| 6,045,790 A | 4/2000 | Campbell ............... 424/93.3 |
| 6,177,082 B1 | 1/2001 | Dowling et al. ......... 424/209.1 |
| 6,398,774 B1 | 6/2002 | Penner et al. .......... 605/514 |
| 6,436,408 B1 | 8/2002 | Dowling et al. ......... 424/209.1 |
| 6,482,414 B1 | 11/2002 | Dowling et al. ......... 424/209.1 |
| 2001/0007860 A1* | 7/2001 | Olsen et al. ........... 514/44 |
| 2002/0156037 A1 | 10/2002 | Volkin et al. .......... 514/44 |
| 2003/0008000 A1 | 1/2003 | Wong et al. ............ 424/450 |

OTHER PUBLICATIONS

Lunn D.P. et al. Antibody responses to DNA vaccination of horses using the influenza virus hemagglutinin gene. Vaccine. May 4, 1999;17(18):2245-58.*

Soboll, G. et al. Regional antibody and cellular immune responses to equine influenza virus infection, and particle mediated DNA vaccination.Vet Immunol Immunopathol. Jul. 15, 2003;94(1-2):47-62.*

(Continued)

*Primary Examiner*—Bruce R. Campell
*Assistant Examiner*—M. Franco Salvoza
(74) *Attorney, Agent, or Firm*—Fellers, Snider, Blankenship, Bailey & Tippens, P.C.

(57) ABSTRACT

The invention is for a DNA vaccine expressing the hemagglutinin (HA1) gene of equine-2 influenza virus. By engineering a stop codon within HA1, expression of HA1 is ensured. By encapsulation of the DNA vaccine in liposome and by intranasal inoculation, it is sufficient to elicit protective immunity at a significantly lower dosage compared to a DNA vaccine expressing the full length HA gene. Lower dosage reduces the risk of induction of anti-DNA antibodies. Intranasal inoculation directly to the respiratory epithelial cells reduces the risk of DNA integration. The inventive vaccine is advantageous over current inactivated or live attenuated vaccines, as updating of the vaccine requires only the replacement of the encoding sequence with the new virus.

18 Claims, 4 Drawing Sheets

OTHER PUBLICATIONS

Nelson, K.M. et al. Local and systemic isotype-specific antibody responses to equine influenza virus infection versus conventional vaccination. Vaccine. Aug. 1998;16(13):1306-13.*

Soboll, G. et al. Mucosal co-administration of cholera toxin and influenza virus hemagglutinin-DNA in ponies generates a local IgA response. Vaccine. Jun. 20, 2003;21(21-22):3081-92.*

Olsen, C.W. DNA vaccination against influenza viruses: a review with emphasis on equine and swine influenza. Vet Microbiol. May 22, 2000;74(1-2):149-64. Review.*

Olsen, C.W. et al. Immunogenicity and efficacy of baculovirus-expressed and DNA-based equine influenza virus hemagglutinin vaccines in mice.Vaccine. Jul. 1997;15(10):1149-56.*

Chen, Z. et al. Enhanced protection against a lethal influenza virus challenge by immunization with both hemagglutinin- and neuraminidase-expressing DNAs. Vaccine. Feb. 26, 1999;17(7-8):653-9.*

Larsen, D.L. et al. Coadministration of DNA encoding interleukin-6 and hemagglutinin confers protection from influenza virus challenge in mice. J Virol. Feb. 1998;72(2):1704-8.*

Invitrogen web page for pcDNA3. 1/V5-His TOPO expression kit; Accessed on Monday, Feb. 28, 2005 at + https://catalog.invitrogen.com/index.cfm?fuseaction=viewCatalog.viewProductDetails&sku=K480040&productDescription=686.*

Kasof, G.M. et al. Btf, a novel death-promoting transcriptional repressor that interacts with Bcl-2-related proteins.Mol Cell Biol. Jun. 1999;19(6):4390-404.*

STIC search of SEQ ID No. 1, Results 1, 5 of .rge.*

STIC search of SEQ ID No. 1, Results 1 (2001), 5 (1996) or .rge (search done Mar. 1, 2005).*

"Diverged Evolution of Recent Equine-2 Influenza (H3N8) Viruses in Western Hemisphere" by Lai et al., Dec. 14, 2000, *Archives of Virology 146* (2001) 1063-1074.

"Alternate Circulation of Recent Equine-2 Influenza Viruses (H3N8) From Two Distinct Lineages in the United States" by Lai et al., *Virus Research 100* (2004) 159-164.

"WHO/OIE Meeting: Consulation on Newly Emerging Strains of Equine Influenza" by Mumford et al., *Vaccine*, vol. 11, Issue 11 (1993) 1172-1175.

"Antigenicity and Immunogenicity of Experimental Equine Influenza ISCOM Vaccines" by Mumford et al., *Vaccine*, vol. 21, Issue 9 (1994) 857-863.

"Protection Against a Lethal Influenza Virus Challenge by Immunization with a Haemagglutinin-Expressing Plasmid DNA" by Robinson et al., *Vaccine*, vol. 11, Issue 9 (1993) 957-960.

"Protection of Ferrets Against Influenza Challenge with a DNA Vaccine to the Haemagglutinin" by Webster et al., *Vaccine*, vol. 12, Issue 16 (1994) 1495-1498.

"Antibody Responses to DNA Vaccination of Horses Using the Influenza Virus Hemagglutinin Gene" by Lunn et al., *Vaccine*, vol. 17 (1999) 2245-2258.

"DNA Vaccines: Protective Immunizations by Parenteral, Mucosal, and Gene-Gun Inoculations" by Fynan et al., *Proc. Natl. Acad. Sci. USA* vol. 90 (1993) 11478-11482.

"Receptor Binding and Membrane Fusion in Virus Entry: The Influenza Hemagglutinin" by Skehel et al., *Annu. Rev. Biochem.* vol. 69 (2000) 531-569.

"DNA Vaccination Against Respiratory Influenza Virus Infection" by Wong et al., *Vaccine*, vol. 19 (2001) 2461-2467.

* cited by examiner

DNA VACCINE EXPRESSING HA1 OF EQUINE-2 INFLUENZA VIRUS

CROSS REFERENCE TO RELATED APPLICATION

This application claims the benefit of copending provisional U.S. patent application Ser. No. 60/470,843, filed May 15, 2003, which application is incorporated herein by reference.

BACKGROUND OF THE INVENTION

1. Technical Field

The present invention relates to vaccines for equine influenza virus, and, more particularly, to a DNA vaccine comprising the HA1 encoding sequence of equine-2 influenza virus which may be administered intranasally of a lower than typical dosage to elicit good mucosal immunity.

2. Background

Equine influenza virus (EIV) is the leading etiological agent for upper respiratory infections in horses. It has been implicated as the cause of epidemic outbreaks of respiratory disease in the horse for centuries. Spread of the virus is rapid and morbidity is extremely high. Infected horses develop typical "flu" symptoms: rapid onset of respiratory distress, coughing, fever, and mucous discharge. In rare cases, fatalities result from secondary bacterial bronchial pneumonia. Although mortality rate is low, the effect of an equine influenza virus infection is significant. It is estimated that the suspension of horse racing in a 1992 Hong Kong outbreak resulted in a loss of US$120 million in revenue. The economic importance in other equine sports may be less, but outbreaks of equine influenza have interrupted international equine events on several occasions. An infected horse without clinical signs but undergoing strenuous training may suffer long term consequences such as reduced pulmonary function. Clinically ill horses suffer the obvious disadvantage of losing training time.

Equine influenza virus is type A influenza virus, a member of Orthomyxoviridae. The viral genome consists of eight segments of negative-stranded RNA. The viral capsid is enclosed in a lipid envelope anchoring two surface viral glycoproteins: hemagglutinin (HA) and neuraminidase (NA). HA is believed to be the most antigenic viral protein of EIV. HA has a molecular weight of approximately 77 kD. This viral protein is synthesized as HA0, and it is cleaved by protease action and subsequent reduction of the single disulfide bond into an amino terminal HA1 portion (50 kD) and a carboxy terminal HA2 portion (27 kD). The HA2 portion is anchored onto the lipid bilayer of a membrane, and HA1 portion is bound to HA2 by non-covalent linkages. The hemagglutinin is involved in binding of the virus to the receptor at the host cell membrane, leading to the subsequent penetration and uncoating of the virus, hence initiating a viral replication. A major goal of vaccination is to induce immunity towards this viral encoded molecule.

There are two subtypes of equine influenza viruses. Type 1, or equine-1 influenza virus (H7N7), has not been isolated in developed countries for the last 15 years. Equine-2 influenza virus (H3N8), however, continues to circulate around the world despite massive vaccination programs. The success of H3N8 virus is probably due to antigenic drift: sequential changes of the antigenicity of HA by amino acid substitution [1]. Recent isolates of equine-2 influenza viruses can be classified into either "American" lineage or "Eurasian" lineage. Furthermore, more recent equine-2 influenza virus has diverged into multiple lineages [2], and that at least in North America, two evolutionary lineages circulate in alternate year [3].

Current EIV vaccines typically consist of formalin or β-propiolactone inactivated whole viruses. The antigenic constituent is composed of equine influenza virus type 1 and type 2. A/Eq/Prague/56 is the only vaccine strain for type 1, whereas, type 2 constituents are the prototype A/Eq/Miami/63 and a later strain such as A/Eq/Kentucky/81 or A/Eq/Fontainebleau/79. A recent meeting of WHO/OIE Consultations on Control of Equine Influenza affirmed the earlier recommendations that vaccines should include both an "American" virus (A/Eq/Kentucky/94) and a "Eurasian" virus (A/Eq/Newmarket/2/93), and that the prototype A/Eq/Miami/63 should be discontinued [4].

In recent prospective study, Morley et. al. [5] have shown that current commercial vaccines do not protect against virus infection, and only have marginal effect in the suppression of clinical symptoms. The lack of protection offered by current commercial vaccines is due to one, or more, of a combination of the following factors:

lack of imununogenicity;
poor choice of vaccine strains; and/or
eliciting an inappropriate immunity.

The continued evolution of equine-2 influenza virus (H3N8) requires periodic updating of the vaccine strain to elicit protective immunity. However, there is a wide spectrum of vaccine strain choices among different vaccine manufacturers.

Immunity generated by an earlier EIV will not be protective against later isolates due to a change of the antigenicity of HA, a result of amino acid substitutions (antigenic drift). This characteristic of the virus is the major obstacle to a "fail-proof" effective vaccine. Updating of vaccine by replacing with more recent virus strains and in a more frequent intervals had been recommended [6]. Some manufacturers still keep outdated virus strains in their products. Although antibodies specific for equine influenza virus are elicited, however, these vaccines are problematic. First, serum antibody level serves as a poor indicator for protection. Second, as the circulating virus strains are sufficiently different from the vaccine strain, there is minimal cross-reactivity. A "partial" immunity elicited by such outdated vaccine renders an infected host a non-symptomatic carrier, that is, the host is infected, but because of the partial immunity, clinical symptoms are suppressed. These infected hosts are not recognized, which facilitates the spread of the virus.

Influenza virus initiates infection by attachment to the ciliated epithelial cells at the upper respiratory tract. Therefore, mucosal antibodies provide an effective defense against the virus. In fact, the importance of nasal antibodies in protection against equine influenza virus has been recognized for many years. In a mouse model, it has been shown that transfer of IgA confers protection against influenza virus infection [7].

Whereas current vaccines elicit serum antibodies, none target mucosal immunity. The correlation between serum antibodies level and vaccine efficacy is unclear, due to the lack of standardization of the measurement for both the antigen and the antibodies [8].

Several strategies, including the use of immune stimulating complexes (ISCOMs) [9], and by direct inoculation to the mucosal area [10], have been used to boost mucosal immune response to current vaccines for equine influenza virus. However, the results showed only limited improvements using these strategies.

A recently licensed vaccine from Heska Corp. (Fort Collins, Colo.), based on recombinant cold-adapted (temperature-sensitive mutant) and attenuated equine influenza virus, is an attempt to elicit mucosal immunity. The vaccine is administered by intranasal inoculation to elicit mucosal immunity. Direct inoculation of cold-adapted attenuated virus to the mucosal site intranasally provides strong stimulation of the mucosal-associated lymphoid tissues (MALT). Therefore, this vaccine is highly immunogenic and elicits mucosal immunity. However, since the vaccine is based on recombinant virus through re-assortment, updating the vaccine requires re-engineering of the cold-adapted attenuated virus. All necessary safety and potency testing has to be done before the updated vaccine can be licensed.

The field of DNA vaccine, or genetic immunization, is a rapidly emerging technology. It was a serendipitous discovery that when a DNA plasmid containing the coding sequences of a protein is injected intramuscularly into a mouse, not only was the antigen expressed, but an immune response to the antigen was also elicited [11, 12]. It is believed that cells take up the DNA plasmid in vivo in a manner similar to that of a DNA transfection in vitro. The DNA plasmid does not replicate inside the host cells, but the encoded antigen is transcribed and translated by the host cell. The antigen is either expressed on the cell surface or secreted, and an immune response is elicited [13]. This new immunization methodolog has been shown to be effective by many investigators, and for a wide spectrum of infectious agents, including influenza virus in general [14], and specific for equine influenza virus [15]. It has been shown that a DNA vaccine expressing the HA gene of A/Eq/Kentucky/81, after administered via skin and mucosa, protected horses against a homologous virus challenge [15].

In the patent art, vaccines and methodologies against EIV are described in U.S. Pat. Nos. 6,482,414; 6,436,408; 6,398,774; 6,177,082; 6,045,790; 4,920,213; 4,693,893; 4,689,224; 4,683,137; 4,631,191; and 4,619,827, all of which are incorporated herein by reference. U.S. Pat. Nos. 4,920,213 and 4,631,191 are directed to recombinant vaccines for immunizing horses against equine influenza virus. DNA sequences encoding the HA and NA glycoproteins from two strains were used to construct vaccinia carried vaccines, to design synthetic peptides for primer and booster administration, and to permit recombinant synthesis of HA and/or NA protein based vaccines.

An ideal vaccine for equine influenza virus, by addressing the above deficiency of current vaccines, should be highly immunogenic, elicit a mucosal immunity, and be amenable to easy "updating".

SUMMARY OF THE INVENTION

The present invention is based on the discovery that a DNA vaccine containing the encoding sequence for the HA1 segment of the HA glycoprotein from equine-2 influenza virus confers protective immunity when administered intranasally. The DNA vaccine expressing HA1 was encapsulated into a liposome vector and inoculated into the nasal cavity of Balb/c mice. After two booster vaccinations, the mice were challenged with a sub-lethal dose of infectious homologous virus. For the non-immunized control group, a 7.9% maximum weight loss was observed. For the DNA vaccine immunized group and for the positive control group (immunized with inactivated homologous virus), the observed weight losses were 1.8% and 1.6%, respectively. In addition, viral specific IgG and IgA antibodies were elicited. The precursor for the HA is cleaved into HA1 and HA2. HA1 is the immunogenic viral glycoprotein, as the antigenic sites are located in this portion of the viral protein. These results described above indicated that the expression of the HA1 alone is sufficient to elicit protective immunity. Furthermore, it was discovered that a much lower dosage of the HA1 DNA vaccine is required to confer protection when compared to a DNA vaccine expressing the full length HA gene.

The DNA vaccine of the present invention possesses other advantages over current inactivated or live attenuated vaccines insofar as updating of the vaccine requires only the replacement of the antigen by inserting the HA1 encoding sequence from a new virus. Moreover, the vaccine can be inoculated intranasally to target for mucosal immunity. The vaccine also can be engineered to optimize the immunogenicity of the expressed antigen.

Another major advantage for the present discovery over prior art in that for the delivery of a DNA vaccine by gene gun, intramuscular, or intradermal injection, there is a risk of integration of the introduced DNA into the chromosome of the host cell. Mutations with adverse results or the development of cancer are potential risks. With intranasal inoculation after liposome encapsulation, the DNA vaccine is delivered directly to the epithelial cells of the respiratory tract. Since epithelial cells are replaced at a high rate, the risk of chromosomal integration is significantly diminished Furthermore, as described below, the use of HA1 alone (with an engineered stop codon) reduces the dosage required, further reducing the risk of integration as well as reducing the risk of eliciting anti-DNA antibodies.

Thus, in one embodiment of the present invention there is provided a DNA vaccine composition comprising DNA encoding sequences for HA1 of equine-2 influenza virus, or epitopes thereof, wherein the vaccine further comprises a pharmacologically acceptable carrier or diluent. The HA1 encoding sequence may be selected from known strains of equine-2 influenza virus, and in one embodiment is preferably from strain A/Eq/Kentucky/98. In a specific example, the HA1 encoding sequence comprises the nucleotide sequence of SEQ ID NO: 1.

In another embodiment of the invention, the DNA vaccine is combined with an adjuvant in order to enhance the immune response and/or to promote the proper rate of absorption following inoculation.

In a further embodiment of the invention, there is provided a method for inducing an immune response in an equine to prevent or reduce the severity of equine influenza virus infection, the method comprising administering to an at-risk animal an effective immunizing amount of the inventive vaccine, alone or in combination with an adjuvant or additional antigenic components or encoding sequences, to provide a means to control equine influenza virus infections, wherein the vaccine further comprises a pharmacologically acceptable carrier or diluent.

Preferably, the DNA vaccine includes a vector, and most preferably, the DNA is encapsulated into liposomes and delivered intranasally into the respiratory tract of the subject in order to elicit a good mucosal immunity.

A better understanding of the present invention and its objects and advantages will become apparent to those skilled in this art from the following detailed description wherein there is described only the preferred embodiment of the invention, simply by way of illustration of the best mode contemplated for carrying out the invention. As will be realized, the invention is capable of modifications in various obvious respects, all without departing from the scope and

DETAILED DESCRIPTION OF THE INVENTION

Figure 1:
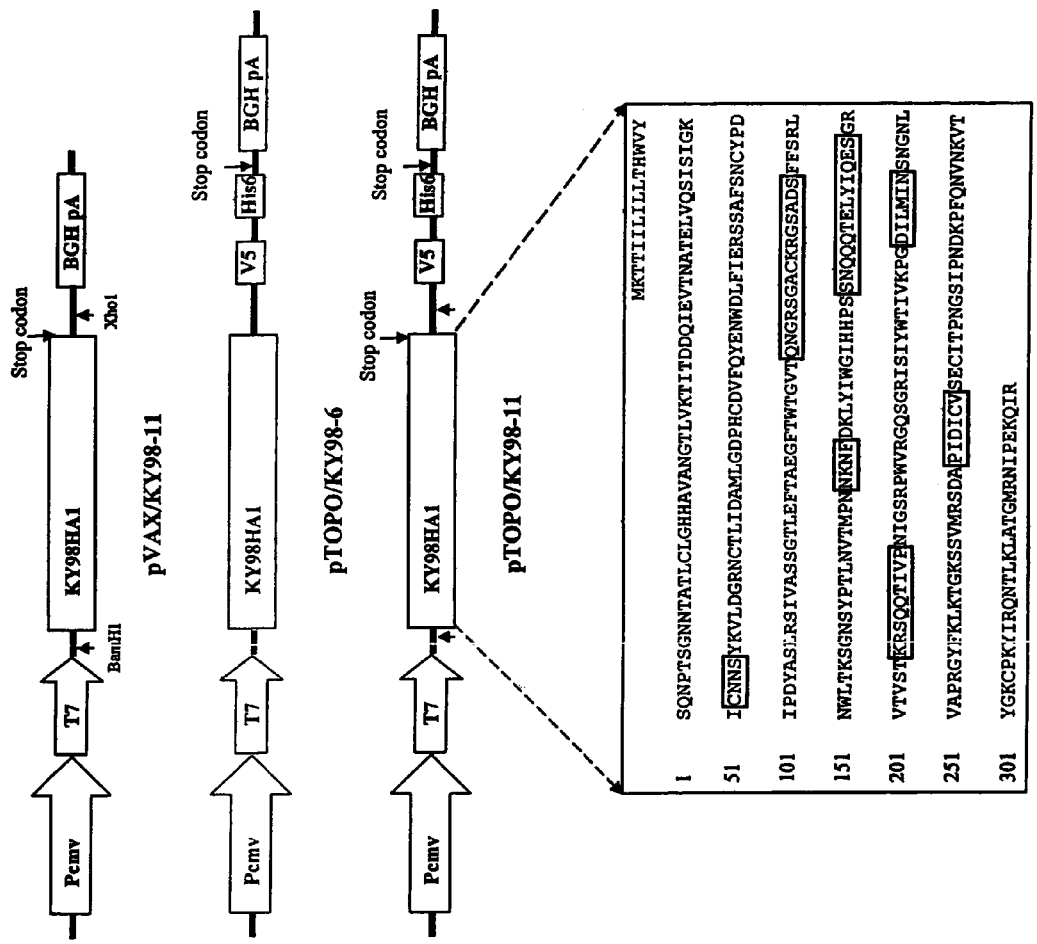
FIG. 1 is a schematic map for example embodiments of the inventive DNA vaccine. The HA1 gene of A/Eq/Kentucky/98 is inserted into a eukaryotic expression vector: either pcDNA3.1/V5-His-TOPO or pVAX1, both being available from Invitrogen (Carlsbad, Calif.). Of the constructed vectors expressing the HA1 of equine-2 influenza virus (A/Eq/Kentucky/98 as an example), pTOPO/KY98-6 utilizes the stop codon provided by the vector, whereas for pTOPO/KY98-11 and pVAX/KY98-11, a stop codon is provided by the reverse primer during PCR. Insert: Amino acid sequence for the HA1 of A/Eq/Kentucky/98 (GenBank Accession No. AF197241). The signal peptide is displayed in the first row. Boxed sequences: Antigenic sites A (132–146); site B (187–199); site C (51–55, 273–278); and site D (171–174, 209–217, 241–246). V5: V5 epitope; His6: Six-histidine tag; BGHpA: Bovine Growth Hormone polyadenylate signal.
Figure 2:
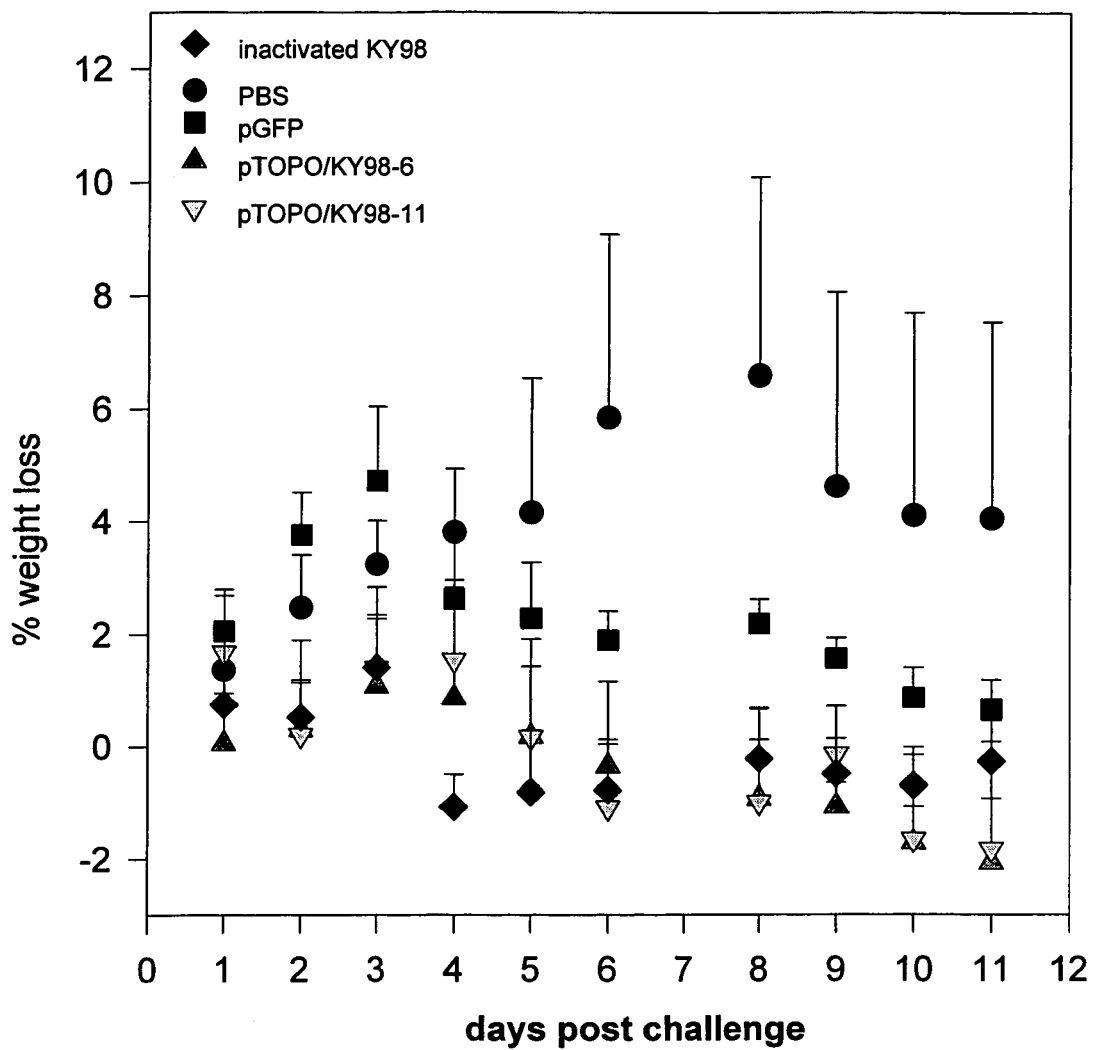
FIG. 2 is a graph reflecting experimental results of the described weight loss study. The percentage weight loss of infected mice is plotted against the days after virus challenge. Inactivated KY98: positive control group; PBS and pGFP: negative control groups. pTOPO/KY98-6 and pTOPO/KY98-11: DNA vaccine immunized groups. The P values for Student's t-test between PBS control group and pTOPO/KY98-6 and pTOPO/KY98-11 immunized groups are 0.001 and 0.006, respectively.

Before explaining the present invention in detail, it is important to understand that the invention is not limited in its application to the details of the construction illustrated and the steps described herein. The invention is capable of other embodiments and of being practiced or carried out in a variety of ways. It is to be understood that the phraseology and terminology employed herein is for the purpose of description and not of limitation.

The present invention provides a novel DNA vaccine and method designed to protect against EIV. The invention is directed to DNA-mediated vaccination and it preferably involves the direct introduction via a vector of isolated DNA encoding HA1 or epitopes thereof selected from any contemporary strain, which is then expressed within cells of the inoculated equid. The inventive vaccine may be administered alone or in combination with additional antigenic components or skilled in the art.

Preferably, the isolated HA1 encoding sequence is selected from the group consisting of strains A/Eq/Kentucky/98, A/Eq/Miami/63, A/Eq/Kentucky/81, A/Eq/Fontainebleau/79, A/Eq/Saskatoon/90, A/Eq/Kentucky/92, A/Eq/Kentucky/94 and A/Eq/Newmarket/2/93, A/Eq/New York/99, A/Eq/Oklahoma/00, and, more preferably, from strain A/Eq/Kentucky/98. Most preferably, the HA1 encoding sequence comprises the nucleotide sequence of SEQ ID NO: 1 from Kentucky/98. But, as contemplated herein, the invention includes the HA1 encoding sequence of other strains and analogs, fragments, mutants, substitutions, synthetics, or variants thereof that effectively encode HA1, its epitopes, and/or mimetics. (See, for example, reference [2] below, Tables 1 and 3, incorporated herein by reference, for a listing of various virus strains with their corresponding GenBank accession numbers, from which the nucleotide sequences of the HA1 gene may be obtained). As a result, the invention encompasses DNA sequences which encode for and/or express in appropriate transformed cells, proteins which may be the full length antigen, antigen fragment, antigen derivative or a fusion product of such antigen, antigen fragment or antigen derivative with another protein. The invention also contemplates a DNA vaccine having an isolated recombinant strain with the immunogenic characteristics of contemporary strains, including the strains herein described.

As defined herein an "isolated" DNA is one which is substantially separated from other cellular components which naturally accompany a native sequence. The term embraces a nucleic acid sequence that has been removed from its naturally occurring environment, and includes recombinant or cloned DNA isolates and chemically synthesized analogs or analogs biologically synthesized.

The term "vector" refers generally to any DNA vaccine vector, numerous ones of which are known in the art, that by itself is "inert" (not eliciting immunity to itself), can easily be introduced to the recipient (to elicit immunity to the insert), and does not integrate into the host chromosome. Reference is made to U.S. Pat. Nos. 6,468,984 and 6,339,068, which patents are incorporated herein and which delineate various vectors and delivery systems known in the art. Preferred vectors are the pVAX1 and pcDNA3.1/V5-His-TOPO eukaryotic expression vectors commercially available from Invitrogen, Carlsbad, Calif.

The vaccine of the present invention may include nucleic acid sequences that regulate the expression of the HA1 encoding sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

The inventive vaccine further comprises a pharmacologically acceptable carrier or diluent. Suitable carriers for the vaccine are well known to those skilled in the art and include but are not limited to proteins, sugars, etc. Such carriers may be aqueous or non-aqueous solutions, suspensions, and emulsions. Examples of non-aqueous carriers are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example antimicrobials, antioxidants, chelating agents, inert gases and the like. Preferred preservatives include formalin, thimerosal, neomycin, polymyxin B and amphotericin B.

The term "adjuvant" refers to a compound or mixture that enhances the immune response and/or promotes the proper rate of absorption following inoculation, and, as used herein, encompasses any uptake-facilitating agent. Acceptable adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and others. A preferred adjuvant is the METASTIM® adjuvant of Fort Dodge Animal Health.

The method comprises administering to the animal an effective immunizing dose of the vaccine of the present invention. For purposes of this invention, an "effective immunizing amount" of the vaccine of the present invention is at least 0.001 µg DNA per kilogram of body weight, and preferably falls within the range of 0.001 µg DNA per kilogram of body weight to 0.01 µg DNA per gram of body weight. The vaccine is preferably administered intranasally, after encapsulation in liposomes/adjuvants as described above, to elicit the desired mucosal immunity, but may otherwise if desired be administered by any of the methods well known to those skilled in the art, for example, by intramuscular, subcutaneous, intraperitoneal, intravenous, orally, intradermal, or ocularly.

The present invention is further illustrated by the following example, which is intended to aid understanding of the invention but is not intended, and should not be construed, to limit in any way the invention as set forth in the claims which follow thereafter.

EXAMPLE

Materials and Methods

Virus and Virus Amplification:

Equine-2 influenza virus, A/Eq/Kentucky/98, was a generous gift from Dr. Thomas Chambers, University of Kentucky. Virus amplification and characterization was performed as previously described [2]. Briefly, the virus was cultivated in 9 to 11 day-old embryonated chicken eggs at 37° C. for 72 hr. The allantoic fluid was harvested as described by Mahr et al. [16]. After clarification by centrifugation at 1000 g for 15 min, virus titer was determined by a hemagglutination assay using chicken erythrocytes.

Construction of DNA Vaccine:

To synthesize the DNA template for cloning, the HA1 open reading frame was prepared by the reverse-transcription and the polymerase chain reaction (RT-PCR). Viral RNA was extracted, and cDNA synthesized using the uni-12 primer (5'AGCAAAAGCAGG3') (SEQ. ID NO: 2) and MMLV reverse transcriptase (Stratagene, La Jolla, Calif.). The template were synthesized by PCR using primers EH3-29+ (5'CATGAAGACAACCATTATTTT3') (SEQ. ID NO: 3) and EH3-1061-(5'TCTGATTTGCTTTTCTGGTA3') (SEQ. ID NO: 4) or EH3-29+ and EH3-1061STOP (5'TCATCTGATTTGCTTTTCTGGTA3') (SEQ. ID NO: 5). PCR was carried out at 95° C., 1 min, 45° C., 2 min, and 72° C., 3 min. for 25 cycles, and using Taq DNA polymerase (Stratagene, La Jolla, Calif.). The PCR product was ligated into pcDNA3.1/V5-His-TOPO eukaryotic vector, according to manufacturer's instructions. Two clones were identified and used in subsequent experiments: pTOPO/KY98-6, and pTOPO/KY98-11 (with a stop codon built in the reverse primer). Expression of the HA1 was confirmed by PCR and by western blot hybridization, using convalescent serum from infected horses. An additional clone, constructed by restriction endonuclease digestion of pTOPO/KY98-11 with BamHI and XhoI to excise the HA1 insert, followed by ligation of the insert into the BamHI and XhoI site of pVAX1, resulting in the creation of pVAX/KY89-11.

DNA Immunization and Virus Challenge:

Plasmid DNA was amplified in *E. coli*, extracted, and purified using a MaxiPrep Kit (Qiagen, Valencia, Calif.). The concentration and purity of the DNA preparation was determined by spectroscopic analysis, and by restriction endonuclease digestion followed by agarose gel electrophoresis. For DNA vaccination, the DNA preparation was diluted in Dulbecco's Modified Eagle's Medium (DMEM) (Roche Applied Science, Indiapolis, Ind.) to 20 μg/ml. The suspension was mixed with an equal volume of lipofectamine (Roche) solution (at 20 μg/ml in DMEM) for 20 min at room temperature before inoculation.

Female Balb/c mice (Jackson Laboratories, Bar Harbor, Me.), 4 to 8 weeks old, were divided into groups of four. For intranasal inoculation, each mouse was anesthetized with isoflurane (forane, 1-choro-2,2,2-trifluoroethyldifluoromethyl ether). With a micropipette, 25.0 μl of the DNA suspension (a dosage of 0.01 μg/g body weight) was instilled into the nasal cavity. Two groups of mice received the DNA vaccine, one with pTOPO/KY98-6, and a second group with pTOPO/KY98-11. Two negative control groups were included. One inoculated with phosphate-buffered saline (PBS) and a second inoculated with a non-related plasmid DNA vector expressing a green fluorescence protein (pGFP/Green Lantern, Gibco, BRL). An additional group was inoculated with uv-inactivated A/Eq/Kentucky/98 at a dosage of 8.0 HA unit (equivalent to $1.6\times10^7$ egg infectious dose 50% [$EID_{50}$], or $1\times10^6$ plague forming unit [pfu]) per mouse as a positive control group. Two booster vaccinations, at the same dosage, were administered on day 21 and on day 35. Virus challenge was given at day 50 (15 days after the second booster). Each mouse was inoculated intranasally with 16 HA unit (equivalent to $3.2\times10^7$ $EID_{50}$, or $2\times10^6$ pfu) of the homologous virus (A/Eq/Kentucky/98), and body weights were measured for each mouse for the next 10 days.

In addition, to investigate if DNA vaccination elicits specific antibodies, sera were collected by retro-orbital bleeding (after anesthesia) at day 0, 21, 35, 50 and 65. These time points correspond to "pre-bled", first and second booster vaccination, virus challenge, and 15 days post-challenge, respectively.

Titration of Viral Specific IgG and IgA:

ELISA plates were prepared by using a suspension of sucrose-gradient purified homologous equine influenza virus, A/Eq/Kentucky/98. The virus was diluted in 50 mM $NaHCO_3$ buffer to 0.6 HA unit/ml, and 100 μl of this virus suspension was added to each well of a ELISA plate. The plates were left at room temperature for 24 hr for the antigen to be "coated" onto the plate. A blocking buffer [PBS containing 2.0% bovine serum albumin (BSA) and 1.0% skim milk] was added after the ELISA plates were washed three times with PBS, and incubated at room temperature for a further hour. One hundred microiter of diluted mouse sera (1:10 in PBS with 2.0% BSA) were added, after washing again with PBS, and incubated as above. Following incubation at room temperature for 1 hr and washing with PBS, 100 μl of diluted (1:2000 in PBS with 2% BSA) alkaline phosphatase-conjugated rabbit anti-murine IgG or IgA antiserum (Sigma, St. Louis, Mo.) was added. After incubation at room temperature for 1 hr, the plates were washed again with PBS, and 100 µl of "substrate" was added [1.0 mg/ml of 4-nitrophenyl phosphate solution (pNPP), Sigma]. After incubation at room temperature for 2.5 hr, absorption at 405 nm was determined using a microplate reader (Biotek Instruments, Winooski, Vt.). All serum samples were assayed in triplicates. The mean absorption for the "pre-bleed" serum was subtracted from the adsorption values of the immune sera, and the results were expressed as an increase in optical density at 405 nm ($\Delta$O.D. 405).

Results

Validation for the DNA Vaccine:

Three DNA vaccine vectors were constructed and identified. They were characterized both by PCR and by restriction digest. PCR and restriction analysis indicated a correct size of insert (approximately 1.0 kb) and correct orientation with respect to the CMV promoter in the pcDNA3.1/V5-His-TOPO and pVAX1 vector, as shown in FIG. 1. The stop codon contained in the EH3-1061STOP primer causes the translation of the HA1 gene insert to terminate before the sequences encoding the V5 epitope and the His6 tag for the vector pTOPO/KY98-11. pVAX/KY98-11 utilizes the "built-in" stop codon within the HA1. Whereas for the vector pTOPO/KY98-6, termination of the insert relies on the stop codon in the vector, hence the product is linked to the V5 and His6 "tag" at its carboxy-terminus. Western blot hybridization using convalescent horse serum demonstrated that both vectors, after transfection into MDBK cells, produced a protein of approximately 50 KD, consistent with the correct expression of the HA1 antigen (data not shown).

DNA Immunization and Virus Challenge:

Since mice do not develop obvious respiratory symptoms characteristic for influenza virus infection, a weight loss model was employed to evaluate the efficacy of the DNA vaccine. Body weight loss after virus challenge and the subsequent recovery were taken as the criteria to compare the severity of symptoms, and hence the level of protection conferred by the DNA vaccine. Each mouse was weighed daily after virus challenge, and the result was expressed as the percentage of body weight change to that of prior to the virus challenge. The mean body weight loss plus the standard error of the mean (SEM) for each group was plotted against days post-infection is shown in FIG. 2.

It was noticeable that the vaccinated mice (with both DNA vaccine vectors or with uv-inactivated virus) developed little or no clinical symptoms such as anorexia, "fluffy coat" appearance (an indicator of pyrexia), and inactivity after virus challenge. For the negative control group immunized with PBS, they showed signs of severe infection, and they started to loose weight on day 1, with a maximum of 7.9% weight loss at day 8 after virus challenge. The weight loss persisted for more than 10 days. The second negative control group (pGFP) also showed significant weight loss for the first 3 days (4.6% body weight), then started to recover. In contrast, none of the immunized groups showed any significant body weight loss.

Paired Student's t-tests were performed on the changes in body weight to determine if there is any statistical significance. The P values for comparing the pTOPOKY98-6 and pTOPOKY98-11 to the PBS control group were 0.001 and 0.006, respectively. This is comparable to the P values of 0.0001 between the positive control group (immunized with uv-inactivated virus) and the PBS group. Therefore, for both DNA vaccine vectors, they elicited a similar protective immunity to that elicited by inactivated virus.

Titration of Viral Specific IgG and IgA:

The result of ELISA is shown in FIGS. 3A and 3B. As described above, the O.D. 405 nm of control sera were deduced, and the result is expressed as the mean of an increased O.D. 405 nm plus the standard error for triplicate wells. Booster vaccinations were administered on days 21 and 35, and the mice were challenged with live virus on day 50. Sera were also tested 15 days after virus challenge.

For the mice immunized with uv-inactivated virus (positive control group), viral specific IgG was detected as early as on day 21, with an increased O.D. of 0.49. (FIG. 3A). However, IgA was detected only marginally, with an increased O.D. of 0.09 (FIG. 3B). On day 35, two weeks after the first booster, IgG level was increased by more than 3-fold. Interestingly, instead of a further increase by the second booster vaccination, the IgG level on day 50 was actually lower than that of on 35. However, after live virus challenge, as expected, there was an increase in IgG level, from O.D. 1.2 to about O.D. 1.7. For IgA, a similar pattern was observed. However, the levels were significantly lower.

For the DNA vaccine immunized groups, both have detectable viral specific IgG and IgA responses and the pattern is similar to that elicited by uv-inactivated virus. After first booster vaccination, there was an increased of 1.5 to 2-fold for IgG and IgA (for pTOPO/KY98-6 vaccinated group, an increased from 0.31 to 0.55, and from 0.17 to 0.36, respectively). Similarly, the second booster vaccination did not raise the levels of IgG or IgA further. However, IgG was increased by more than 3-fold after virus challenge. IgA was also elevated, although less than 2-fold.

Interestingly, for the negative control group vaccinated with a non-specific vector, pGFP, viral specific IgG or IgA before virus challenge was "detected". However, an increase of less than 0.2 O.D. may be a non-specific result. After virus challenge, both IgG and IgA were detected, as expected in a primary infection (FIG. 3A and FIG. 3B). Similarly, for the PBS immunized group, the O.D. for IgG and IgA at 15 days post virus challenge were 1.68±0.12 and 0.35±0.03, respectively (data not shown).

Discussion

Less DNA for the Protection

Influenza virus has been used as a model organism in the study of DNA vaccines. As early as 1993, it has been shown that an HA expressing plasmid could confer protection against influenza [17] [18] [19] [13]. However, these investigations were done using a DNA construct consisted of the full length HA gene. The HA is the viral glycoprotein for receptor binding and membrane fusion, and the bulk of the HA2 molecule is an integral membrane protein. The hemagglutinin is synthesized as an HA0 precursor, followed by proteolytic cleavage into HA1 and HA2. HA1 contains the major protective antigenic sites, and it is non-covalently linked to HA2 which is anchored into the viral envelope [20]. We report here that, with the expression of HA1 alone is sufficient to elicit protective immunity. Omission of the HA2 may circumvent a requirement for enzymatic processing, as a tissue specific protease is required to cleave the precursor HA0 into HA1 and HA2. Furthermore, in the absence of HA2, synthesized HA1 will not be membrane bounded, and hence allowing more HA1 molecules to be released and taken up by antigen presenting cells to elicit a stronger immune response. Therefore, the immunogenicity of this DNA vaccine is significantly enhanced. In addition, a lower quantity of this DNA vaccine is required for immunization. Protective immunity was elicited by as low as 0.01 µg DNA per gram of body weight, which is 10-fold less than that reported by Wong et al. [21], and is a 2-fold less than used by a gene gun inoculation [17]. It should be noted that, if the same dosage as reported by Fynan et al. were applied for a horse with an average size of 400 Kg, the amount of DNA required would be 4.0 mg per inoculation.

Furthermore, by encapsulating a DNA vaccine, immunization with less DNA, and by inoculation at mucosal site, the risk of potential DNA integration into somatic or germline cells is significantly reduced.

Role of IgA

Influenza virus initiates infection at the respiratory tract. As many previous studies have shown, mucosal immunity is important in protection against influenza virus or other respiratory infections [22, 23]. Secretory IgA plays a significant role in mucosal immunity. It has been shown that IgA is responsible for the protection against influenza virus infection [24]. Furthermore, passive transfer of influenza-specific IgA protects the recipient mice from influenza virus infection [7]. Lunn et al. had investigated a DNA vaccine for equine influenza virus in ponies [15]. Using a gene gun, a DNA vaccine was delivered to several mucosal sites, including the tongue, conjunctiva, and the third eyelid. In each case, a strong IgG response was stimulated. However, a poor IgA response was elicited.

The results indicate that by encapsulation of the DNA vaccine into liposomes and by delivering the DNA vaccine into the respiratory tract, a better mucosal immunity is elicited. The protection is probably mediated by IgA at the respiratory tract (a mucosal site), as there was a corresponding increased in serum viral specific IgA.

Booster and Non-specific Immunity

The results suggest that a second booster may not be necessary, as this did not result in an increase in the titers of viral specific IgG or IgA. Possibly, the titer after the first booster vaccination might have remained for several weeks, rendering the second booster unnecessary. Alternatively, the presence of viral specific antibodies neutralized further antigens introduced by the second booster vaccination.

Figure 3A:
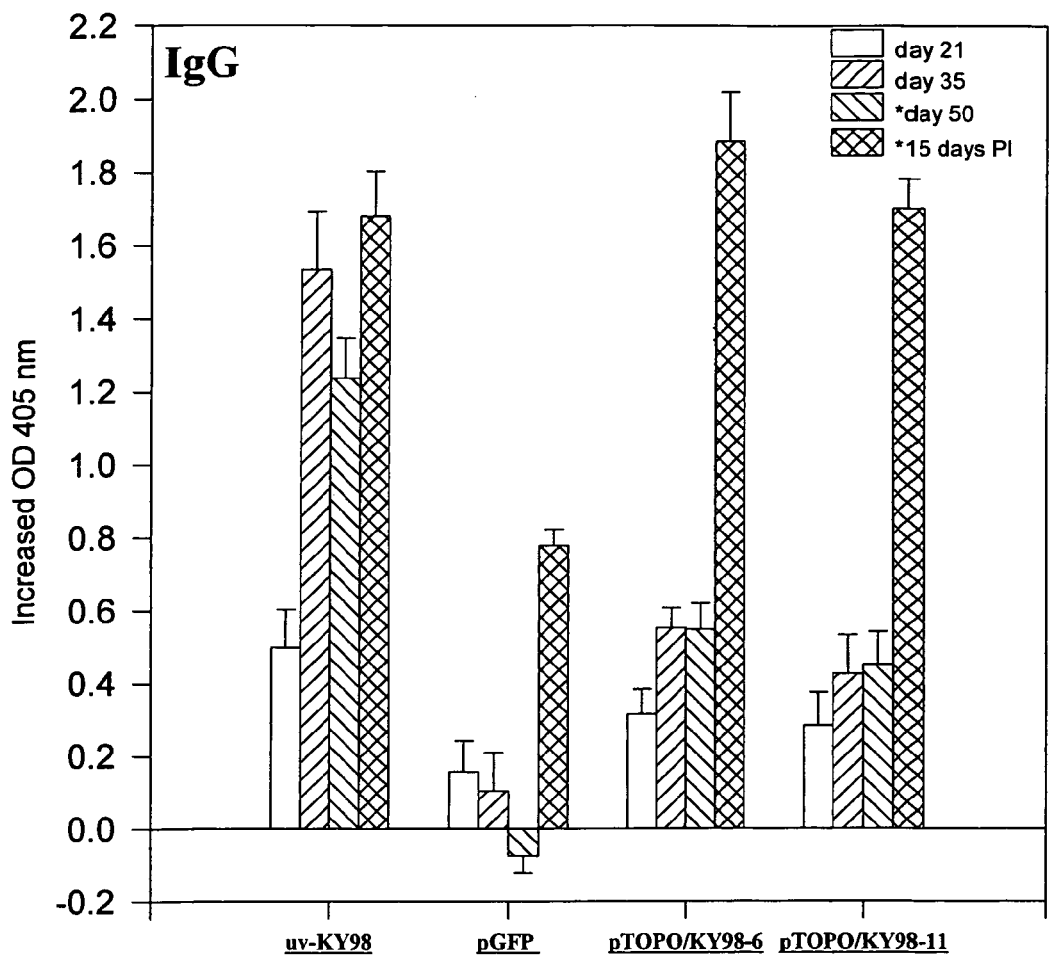
FIG. 3A is a graph reflecting experimental results of the described ELISA for serum viral specific IgG. Boosters were administrated on day 21 and day 35. Virus challenge was administered 15 days after the second booster on day 50, and 15 days post infection, as indicated by*.
Figure 3B:
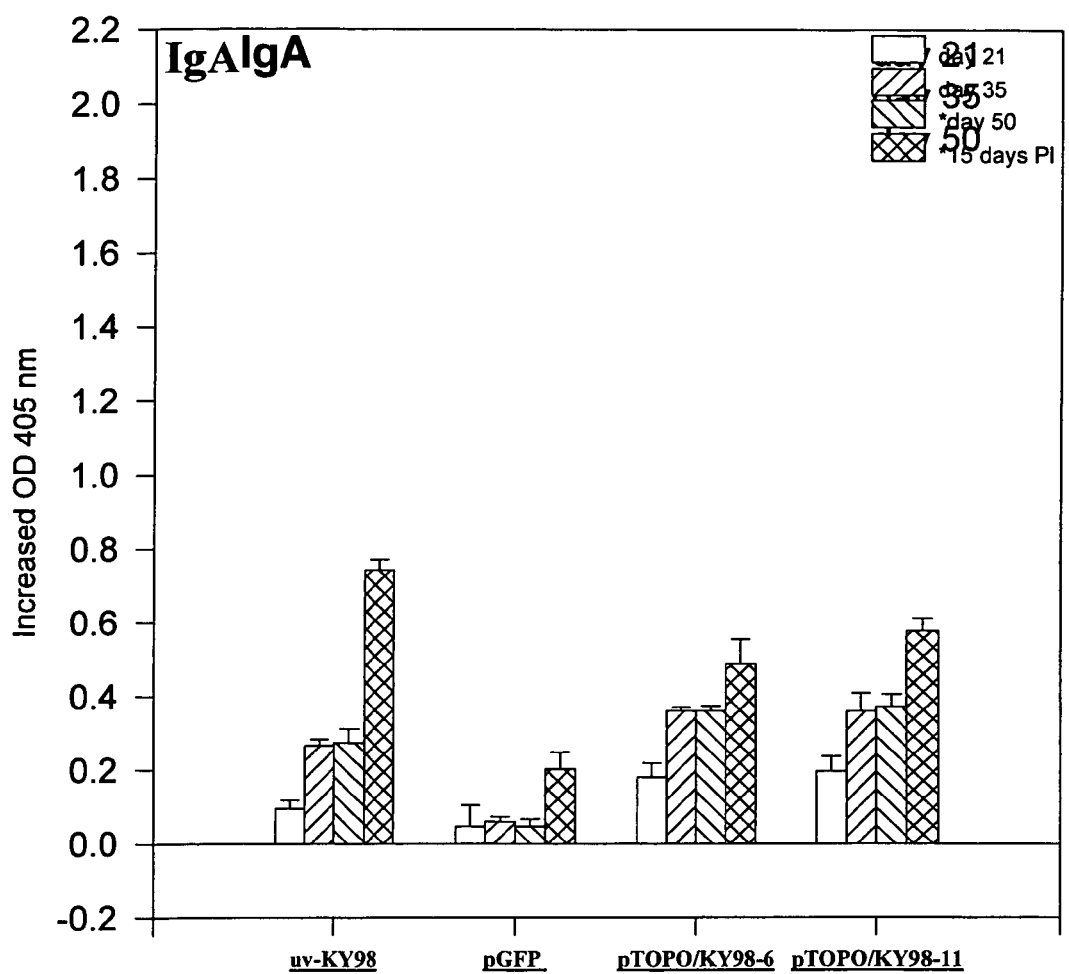
FIG. 3B is another graph reflecting experimental results of the described ELISA for serum viral specific IgA. Boosters were administrated on day 21 and day 35. Virus challenge was administered 15 days after the second booster on day 50, and 15 days post infection, as indicated by*.

Interestingly, IgG level was increased by more than 3-fold after virus challenge for both DNA vaccinated groups (FIG. 3A, for both pTOPOKY98-6 and pTOPOKY98-11). In contrast, the increased was less than 1-fold for uv-inactivated virus. This observation is comparable to previously reports by others that a DNA vaccine elicits good priming responses. This "anamnesty" response by the DNA vaccine is probably due to the differences in the kinetics and the pathway of antigen presentation to that elicited by an inactivated antigen. Furthermore, it is difficult to determine the true quantity of available antigen for the induction of immune response by a DNA vaccine, the mechanism for this enhanced "priming effect" by a DNA vaccine remains to be elucidated.

It is also interesting to note that, for the mice immunized with pGFP (used as negative control), weight loss peaked at day 3, and began to recover by day 4, significantly earlier than the other negative control group (PBS). A paired Student's t-test to the PBS group resulted in a P value of 0.033. However, these mice had similar clinical features as the PBS control group. Furthermore, the weight loss was comparable to the PBS group for the first 3 days post virus challenge. If the criterion for a true protection is to have no clinical symptoms at all, these mice were not "protected", even though the P value is significant. This "earlier recovery" is not due to specific immunity, as no viral specific antibodies were detected prior to virus challenge (the absorbance values were bordering at the background level). It is well known that certain motifs in a DNA vaccine vector elicit non-specific immunity. Introduction of liposomes at the mucosal site might also induce a non-specific immunity.

Additional Data

To establish a protocol for mucosal immunization in the horse, several horses were inoculated intranasally with the DNA vaccine of the present invention, and nasal washings collected several weeks later revealed positive signals for viral specific antibodies.

BIBLIOGRAPHY

The following publications are incorporated herein by reference:

1. Daly J M, Lai A C, Binns M M, Chambers T M, Barrandeguy M, Mumford J A: Antigenic and genetic evolution of equine H3N8 influenza A viruses. *J Gen Virol* 1996, 77 (Pt4):661–671.
2. Lai A C, Chambers T M, Holland R E, Jr., Morley P S, Haines D M, Townsend H G, Barrandeguy M: Diverged evolution of recent equine-2 influenza (H3N8) viruses in the Western Hemisphere. *Arch Virol* 2001, 146:1063–1074.
3. Lai A C, Rogers K M, Glaser A, Tudor L, Chambers T: Alternate circulation of recent equine-2 influenza viruses (H3N8) from two distinct lineages in the United States. *Virus Res* 2004, 100:159–164.
4. Mumford J, Wood J: WHO/OIE meeting: consultation on newly emerging strains of equine influenza. 18–19 May 1992, Animal Health Trust, Newmarket, Suffolk, UK. *Vaccine* 1993, 11:1172–1175.
5. Morley P S, Townsend H G, Bogdan J R, Haines D M: Efficacy of a commercial vaccine for preventing disease caused by influenza virus infection in horses [see comments]. *J Am Vet Med Assoc* 1999, 215:61–66.
6. Mumford J A: The equine influenza surveillance program. *Adv Vet Med* 1999, 41:379–387.
7. Renegar K B, Small P A, Jr.: Passive transfer of local immunity to influenza virus infection by IgA antibody. *J Immunol* 1991, 146:1972–1978.
8. Mumford J A, Wood J: Establishing an acceptability threshold for equine influenza vaccines. *Dev Biol Stand* 1992, 79:137–146.
9. Mumford J A, Jessett D, Dunleavy U, Wood J, Hannant D, Sundquist B, Cook R F: Antigenicity and immunogenicity of experimental equine influenza ISCOM vaccines. *Vaccine* 1994, 12:857–863.
10. Kuno-Sakai H, Kimura M, Ohta K, Shimojima R, Oh Y, Fukumi H: Developments in mucosal influenza virus vaccines. *Vaccine* 1994, 12:1303–1310.
11. Tang D C, DeVit M, Johnston S A: Genetic immunization is a simple method for eliciting an immune response. *Nature* 1992, 356:152–154.
12. Donnelly J J, Ulmer J B, Liu M A: Immunization with DNA. *J Immunol Methods* 1994, 176:145–152.
13. Robinson H L, Hunt L A, Webster R G: Protection against a lethal influenza virus challenge by immunization with a haemagglutinin-expressing plasmid DNA. *Vaccine* 1993, 11:957–960.

14. Webster R G, Fynan E F, Santoro J C, Robinson H: Protection of ferrets against influenza challenge with a DNA vaccine to the haemagglutinin. *Vaccine* 1994, 12:1495–1498.
15. Lunn D P, Soboll G, Schram B R, Quass J, McGregor M W, Drape R J, Macklin M D, McCabe D E, Swain W F, Olsen C W: Antibody responses to DNA vaccination of horses using the influenza virus hemagglutinin gene. *Vaccine* 1999, 17:2245–2258.
16. Mahy B, Kangro, H O: *Virological Methods Manual*: Academy Press, Harcourt Brace & Company, Publishers; 1996.
17. Fynan E F, Webster R G, Fuller D H, Haynes J R, Santoro J C, Robinson H L: DNA vaccines: protective immunizations by parenteral, mucosal, and gene-gun inoculations. *Proc Natl Acad Sci USA* 1993, 90:11478–11482.
18. Fynan E F, Robinson H L, Webster R G: Use of DNA encoding influenza hemagglutinin as an avian influenza vaccine. *DNA Cell Biol* 1993, 12:785–789.
19. Montgomery D L, Shiver J W, Leander K R, Perry H C, Friedman A, Martinez D, Ulmer J B, Donnelly J J, Liu M A: Heterologous and homologous protection against influenza A by DNA vaccination: optimization of DNA vectors. *DNA Cell Biol* 1993, 12:777–783.
20. Skehel J J, Wiley D C: Receptor binding and membrane fusion in virus entry: the influenza hemagglutinin. *Annu Rev Biochem* 2000, 69:531–569.
21. Wong J P, Zabielski M A, Schmaltz F L, Brownlee G G, Bussey L A, Marshall K, Borralho T, Nagata L P: DNA vaccination against respiratory influenza virus infection. *Vaccine* 2001, 19:2461–2467.
22. Ada G L, Jones P D: The immune response to influenza infection. *Curr Top Microbiol Immunol* 1986, 128:1–54.
23. Freihorst J, Ogra P L: Mucosal immunity and viral infections. *Ann Med* 2001, 33:172–177.
24. Liew F Y, Russell S M, Appleyard G, Brand C M, Beale J: Cross-protection in mice infected with influenza A virus by the respiratory route is correlated with local IgA antibody rather than serum antibody or cytotoxic T cell reactivity. *Eur J Immunol* 1984, 14:350–356.

In view of the above, it will be seen that the several objectives of the invention are achieved and other advantageous results attained. As various changes could be made without departing from the scope of the invention, it is intended that all matter contained in the above description or shown in the accompanying drawings shall be interpreted as illustrative and not in a limiting sense. While the invention has been described with a certain degree of particularity, it is understood that the invention is not limited to the embodiment(s) set for herein for purposes of exemplification, but is to be limited only by the scope of the attached claim or claims, including the full range of equivalency to which each element thereof is entitled.

What is claimed is:

1. A vaccine for equine influenza virus, comprising:
an effective immunizing amount of an isolated DNA, the isolated DNA comprising sequences that encode at least a fragment of an HA1 protein, wherein DNA encoding HA2 is absent, the sequences being from a strain of equine-2 influenza virus; and a pharmacologically acceptable carrier or diluent.

2. The vaccine according to claim 1, wherein the strain of equine-2 influenza virus is selected from the group consisting of A/Eq/Kentucky/98, A/Eq/Miami/63, A/Eq/Kentucky/81, A/Eq/Fontainebleau/79, A/Eq/Kentucky/94, A/Eq/Newmarket/2/93, A/Eq/New York/99, and A/Eq/Oklahoma/2000.

3. The vaccine according to claim 1, wherein the strain is A/Eq/Kentucky/98.

4. The vaccine according to claim 1, wherein the sequences that encode at least a fragment of an HA1 protein, wherein DNA encoding HA2 is absent, comprise the nucleotide sequence of SEQ ID NO: 1.

5. The vaccine according to claim 1, further comprising one or more of the group consisting of additional antigenic components, encoding sequences for additional antigenic components, and other vaccines.

6. The vaccine according to claim 1, further comprising a vector containing the sequences that encode at least a fragment of an HA1 protein, wherein DNA encoding HA2 is absent.

7. The vaccine according to claim 6, wherein the vector is a eukaryotic expression vector.

8. The vaccine according to claim 7, wherein the vector is selected from the group consisting of pcDNA3.1/V5-His-TOPO and pVAX1.

9. The vaccine according to claim 1, further comprising an adjuvant.

10. The vaccine according to claim 9, wherein the adjuvant is selected from the group consisting of complete Ereund's adjuvant, incomplete Freund's adjuvant, saponin, mineral gels, surface active substances, pluronic polyols, polyanions, peptides, oil or hydrocarbon emulsions, keyhole limpet hemocyanins, and dinitrophenol.

11. The vaccine according to claim 1, further comprising a liposome into which the sequences that encode at least a fragment of an HA1 protein, wherein DNA encoding HA2 is absent is encapsulated.

12. A method of inducing an immune response against equine influenza virus, comprising administering to an equip an effective immunizing amount of the vaccine of claim 1.

13. The method according to claim 12, further comprising the steps of inserting the sequences that encode at least a fragment of an HA1 protein, wherein DNA encoding HA2 is absent into a vector and delivering the vaccine intranasally into the respiratory tract.

14. The method according to claim 13, wherein the vector is a eukaxyotic vector.

15. The meted according to claim 14, wherein the vector is selected from the group consisting of pcDNA3.1/V5-His-TOPO and pVAX1.

16. The method according to claim 14, wherein the vector is a liposome.

17. The method according to claim 12, wherein the vaccine is administered at a dosage of at least 0.01 µg DNA per gram of body weight.

18. The method according to claim 12, wherein the vaccine is administered at a dosage falling within the range of 0.001 µg DNA per kilogram of body weight to 0.01 µg DNA per grain of body weight.

* * * * *

UNITED STATES PATENT AND TRADEMARK OFFICE
CERTIFICATE OF CORRECTION

PATENT NO. : 7,244,435 B2
APPLICATION NO. : 10/826929
DATED : July 17, 2007
INVENTOR(S) : Lai It is certified that error appears in the above-identified patent and that said Letters Patent is hereby corrected as shown below:

- Column 16, line 66 the word "Eruend's" should be --Freund's--

- Column 17, line 8 the word "equip" should be --equid--

- Column 17, line 16 the word "eukaxyotic" should be --eukaryotic--

- Column 18, line 1 the word "meted" should be --method--

- Column 18, line 14 the word "grain" should be --gram--

Signed and Sealed this

Sixteenth Day of October, 2007

JON W. DUDAS
*Director of the United States Patent and Trademark Office*

```
                             SEQUENCE LISTING

<160> NUMBER OF SEQ ID NOS: 5

<210> SEQ ID NO 1
<211> LENGTH: 1061
<212> TYPE: DNA
<213> ORGANISM: A/Eq/Kentucky/98

<400> SEQUENCE: 1
agcaaaagca ggggatattt ctgtcaatca tgaagacaac cattattttg atactactga      60
cccattgggt ctacagtcaa aacccaacca gtggaaacaa cacagccaca ttatgtctgg     120
gacaccatgc agtagcaaat ggaacattgg taaaaacaat aactgatgac caaattgagg     180
tgacaaatgc tactgaatta gttcagagca tttcaatagg gaaaatatgc aacaactcat     240
ataaagttct agatggaaga aattgcacat taatagatgc aatgctagga gaccccact      300 gtgatgtctt ccagtatgag aatttggacc tcttcataga aagaagcagc gctttcagca     360
attgctaccc atatgacatc cctgactatg catcgctccg gtccattgta gcatcctcag     420
gaacattaga attcacagca gagggattca catggacagg tgtcactcaa aacggaagaa     480
gtggagcctg caaaaggga tcagccgata gtttctttag ccgactgaat tggctaacaa     540
aatctggaaa ctcttacccc acattgaatg tgacaatgcc taacaataaa aatttcgaca     600
aactatacat ctgggggatt catcacccga gctcaaacca acagcagaca gaattgtaca     660
tccaagaatc aggacgagta acagtctcaa caaaaagaag tcaacaaacg atagtcccta     720
atatcggatc tagaccgtgg gttaggggtc aatcaggcag gataagcata tactggacca     780
ttgtaaaacc tggagatatc ctaatgataa acagtaatgg caacttagtt gcaccgcggg     840
gatattttaa attgaaaaca gggaaaagct ctgtaatgag atcagatgca cccatagaca     900
tttgtgtgtc tgaatgtatt acaccaaatg gaagcatccc caacgacaaa ccatttcaaa     960
```

```
atgtgaacaa agttacatat ggaaaatgcc ccaagtatat caggcaaaac actttaaagc    1020
tggccactgg gatgaggaat ataccagaaa agcaaatcag a                        1061

<210> SEQ ID NO 2
<211> LENGTH: 12
<212> TYPE: DNA
<213> ORGANISM: artificial sequence
<220> FEATURE:
<223> OTHER INFORMATION: oligonucleotide primer

<400> SEQUENCE: 2
agcaaaagca gg                                                          12

<210> SEQ ID NO 3
<211> LENGTH: 21
<212> TYPE: DNA
<213> ORGANISM: artificial sequence
<220> FEATURE:
<223> OTHER INFORMATION: oligonucleotide primer

<400> SEQUENCE: 3
catgaagaca accattattt t                                                21

<210> SEQ ID NO 4
<211> LENGTH: 20
<212> TYPE: DNA
<213> ORGANISM: artificial sequence
<220> FEATURE:
<223> OTHER INFORMATION: oligonucleotide primer

<400> SEQUENCE: 4
tctgatttgc ttttctggta                                                  20

<210> SEQ ID NO 5
<211> LENGTH: 23
<212> TYPE: DNA
<213> ORGANISM: artificial sequence
<220> FEATURE:
<223> OTHER INFORMATION: oligonucleotide primer

<400> SEQUENCE: 5
tcatctgatt tgcttttctg gta                                              23
```